(12) United States Patent
Chang et al.

(10) Patent No.: US 8,808,714 B2
(45) Date of Patent: Aug. 19, 2014

(54) USE OF A MIXTURE OF TWO OR MORE ENTERIC MATERIALS TO REGULATE DRUG RELEASE VIA MEMBRANE OR MATRIX FOR SYSTEMIC THERAPEUTICS

(75) Inventors: Rong-Kun Chang, Rockville, MD (US); Niraj Shah, Owings Mills, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 43 days.

(21) Appl. No.: 12/929,238

(22) Filed: Jan. 10, 2011

(65) Prior Publication Data

US 2011/0212156 A1    Sep. 1, 2011

Related U.S. Application Data

(63) Continuation of application No. 10/751,766, filed on Jan. 5, 2004, now Pat. No. 7,910,128.

(60) Provisional application No. 60/437,800, filed on Jan. 3, 2003.

(51) Int. Cl.
*A61K 9/00* (2006.01)
*A61F 13/00* (2006.01)

(52) U.S. Cl.
USPC .......................................... 424/400; 424/443

(58) Field of Classification Search
None
See application file for complete search history.

(56) References Cited

U.S. PATENT DOCUMENTS

| | | | |
|---|---|---|---|
| 4,980,170 A | 12/1990 | Schneider et al. | |
| 6,068,859 A | 5/2000 | Curatolo et al. | |
| 6,565,877 B1 | 5/2003 | Mukherji et al. | |
| 6,893,661 B1 | 5/2005 | Odidi et al. | |
| 7,374,779 B2 * | 5/2008 | Chen et al. | 424/451 |
| 2003/0180352 A1 | 9/2003 | Patel et al. | |
| 2004/0023848 A1 | 2/2004 | Boehm | |
| 2005/0163842 A1 * | 7/2005 | Boehm et al. | 424/468 |
| 2005/0271708 A1 | 12/2005 | Thombre | |
| 2006/0134196 A1 | 6/2006 | Rosenberg et al. | |
| 2006/0240105 A1 * | 10/2006 | Devane et al. | 424/470 |
| 2008/0124393 A1 | 5/2008 | Swanson et al. | |
| 2009/0136593 A1 | 5/2009 | Konofal | |
| 2009/0317471 A1 | 12/2009 | Naringrekar et al. | |
| 2010/0160363 A1 | 6/2010 | Cardinal et al. | |

FOREIGN PATENT DOCUMENTS

| | | |
|---|---|---|
| EP | 0 348 808 B1 | 1/1990 |
| WO | WO 99/29305 A1 | 6/1999 |
| WO | WO 01/66094 A1 | 9/2001 |
| WO | WO 02/17887 A1 | 3/2002 |
| WO | WO 2004/026314 A1 | 4/2004 |

OTHER PUBLICATIONS

Khan et al. (Drug development and Industrial Pharmacy, 26(5), 549-554 (2000)).*
International Search Report and Written Opinion mailed May 23, 2011, in corresponding PCT/US2011/030442, 10 pages.
Supplementary Partial European Search Report dated Nov. 7, 2007, in corresponding European application EP 04 700 220.9, 4 pages.
Office Action dated Feb. 26, 2009, in corresponding European application EP 04 700 220.9, 3 pages.
Khan et al., "A PH-dependent colon targeted oral drug delivery system using methacrylic acid copolymers—Manipulation of drug release using Eudragit® S100 combinations," Journal of Controlled Release, Mar. 29, 1999, 58(2):215-222.
Maulding et al., "Sovolysis of a Substitute Imidazoline, Mazindol," Journal of Pharmaceutical Sciences, Nov. 1975, 64(11):1833-1838.

* cited by examiner

*Primary Examiner* — Snigdha Maewall
(74) *Attorney, Agent, or Firm* — Foley & Lardner LLP; Sunit Talapatra

(57) ABSTRACT

Disclosed are pharmaceutical compositions, particularly oral dosage forms, which comprise two or more enteric coating materials, either as a coating or as part of a matrix dosage form, and methods of making and using the same. The compositions are characterized by having a sustained release profile at lower pH and an accelerated dissolution profile at higher pH.

13 Claims, No Drawings

US 8,808,714 B2

USE OF A MIXTURE OF TWO OR MORE ENTERIC MATERIALS TO REGULATE DRUG RELEASE VIA MEMBRANE OR MATRIX FOR SYSTEMIC THERAPEUTICS

This nonprovisional application claims the benefit of U.S. Provisional Application No. 60/437,800, filed Jan. 3, 2003, the entirety of which is incorporated herein by reference.

FIELD OF THE INVENTION

The present invention is directed to pharmaceutical compositions, particularly oral dosage forms, and methods of making and using the same. The compositions are characterized by having a sustained release profile at lower pH and an accelerated dissolution profile at higher pH.

BACKGROUND OF THE INVENTION

Most drugs given orally are tablets or capsules containing beads, which must dissolve before absorption through the intestinal wall can occur. It is sometimes desirable in the case of a particular drug or a particular therapeutic situation to control the dissolution of the dosage form, i.e. prepare it such that it is immediately-released, or its release is delayed or sustained to maintain certain plasma levels.

In general, drug absorption is relatively slow in the stomach, becomes rapid in the small intestine, and sharply declines in the large intestine. Oftentimes, this drug absorption difference in various gastrointestinal segments is ignored when designing a drug product. For example, an oral drug product with a pH-independent, zero-order dissolution profile is commonly considered ideal. However, this type of product design may suffer from a lower bioavailability, due to the entombment of the drug in fecal material and the low absorption in the large intestine. That is, a significant portion of the drug may still be present after passing through the small intestine, and that portion does not have a good chance of being absorbed. The large intestine is concerned primarily with absorption of water and the secretion of mucous to aid the intestinal contents to slide down the intestinal tube. Because of a low absorptive area and lack of villi/microvilli structures, the absorption of nutrients and drugs is not the major function of the large intestine. A high amount of undissolved drug in the large intestine may lead to a significant bioavailability reduction.

Compensation for changing absorption characteristics in the gastrointestinal track may be important for some drugs. It is rational for a delivery system to pump out the drug much faster when the system reaches the distal segment of the intestine to avoid the drug entrapment in the feces. By using a combination of two or more enteric materials to form a membrane-controlled or a matrix-controlled dosage form, the duration of a drug can be prolonged and the amount of the unabsorbed drug in the lower intestine, due to the entrapment of the drug and sharply declining absorption characteristics in large intestine, can be minimized.

The present invention provides formulations designed to optimize (i.e. accelerate) absorption in the small intestine in order to overcome this problem of "dose-dumping".

While there are numerous formulations for sustained release and delayed release, it is believed that the present inventors for the first time address the problem of poor bioavailability of a drug or drugs in an oral dosage form due to pH changes in the intestinal lumen. As mentioned above, prior controlled release forms were focused on maintenance of blood levels of the active substance or substances, either for therapeutic purposes or to reduce side effects. For instance, U.S. Pat. No. 6,068,859, discloses controlled-release oral dosage forms that will reduce side effects, which are made in such a manner that most of the drug is released distal to the duodenal portion of the small intestine. One alternative disclosed therein is the preparation of an oral dosage form that combines sustained release properties with delayed release characteristics for the drug, azithromycin. This approach gives a sustained released profile after an enteric delay period. The sustained release properties, however, are not pH-dependent. In other words, the system failed to provide an accelerated dissolution profile at higher pH and may suffer a significant bioavailability loss if the active pharmaceutical ingredient in the system has low permeability in the lower gastrointestinal tract.

SUMMARY OF THE INVENTION

It is an object of the present invention to provide a pharmaceutical composition with improved bioavailability of the active ingredient (or ingredients), in which the majority of the active agent therein is released and absorbed prior to entering the large intestine. By majority is meant more than half. It is desirable to have more than about 75% of the active agent released and absorbed in the small intestine.

It is also an object of the present invention to provide a pharmaceutical composition, which displays a sustained release profile at lower pH and an accelerated dissolution profile at high pH. More particularly, this pharmaceutical composition will have a sustained release profile of the active ingredient(s) in a first portion of the small intestine and an accelerated release profile in the second portion of the small intestine.

Another object of the present invention is the preparation of the pharmaceutical compositions described above.

Still another object of the present invention is a method of delivery of the pharmaceutical compositions of the present invention to a patient in need of the active ingredient or ingredients contained therein.

DETAILED DESCRIPTION OF THE INVENTION

In accordance with one aspect of the present invention, provided is a pharmaceutical composition, which comprises a core that contains one or more pharmaceutically active ingredients, and a coating layer surrounding the core, wherein the coating layer comprises a combination of two or more enteric coating materials, at least two of which are materials that will dissolve at different pH's. Thus, the release profile of the active ingredient(s) of the core is pH-dependent.

By "pharmaceutical composition" is meant one or more pharmaceutically active ingredients in combination with other materials that make it suitable for administration to a "patient" (human or other mammal) for therapeutic or nutritional purposes. The "core" contains the active ingredient(s) and is prepared by processes known in the art by combining the active ingredient(s) with other ingredients such as fillers, binders and other customary excipient ingredients, depending in part on the dosage form intended, and formed into tablets, beadlets, pellets and/or granules or other particles. It will be understood that when the term "ingredient" is used herein, it may refer to a singular substance or two or more substances.

A coating containing two or more enteric materials surrounds the core. 'Enteric materials" are polymers that are substantially insoluble in the acidic environment of the stomach, but are predominantly soluble in intestinal fluids at specific pHs. The enteric materials are non-toxic, pharmaceutically acceptable polymers, and include, for example, cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The foregoing is a list of possible materials, but one of skill in the art would recognize that it is not comprehensive and that there are other enteric materials that would meet the objectives of the present invention of providing for a sustained/accelerated release profile. The coating contains two or more enteric polymers that are soluble at different pHs. These solubilities are either known or readily determinable in vitro. Hydroxypropyl methylcellulose phthalate (HPMCP), polyvinyl acetate phthalate (PVAP) and Coateric will dissolve in buffers of pH 5.0 and higher. Eudragit L100-55, Eudragit L30D-55, Kollicoat EMM30D, and Estacryl 30D will dissolve from pH5.5 to 6.5. Cellulose acetate phthalate (CAP) and Aquateric will dissolve in buffers above pH 6.2. Eudragit S100 and FS30D will dissolve around pH7.0-7.5. Roughly, the pH of the duodenum is about 5.5, the jejunum is about 6.5 and the distal ileum is about 7.5.

The coating has at least two enteric materials in it to ensure the desired release profile. For example, with a coating comprising HPMCP and Eudragit FS30D, the HPMCP will begin to dissolve in the duodenum, but the core will still be coated with the Eudragit FS30D and so will give a sustained release of the drug in that time period that the dosage unit is in the first portion of the small intestine. However, when the dosage unit reaches the distal jejunum and ileum portion, the Eudragit FS30D will dissolve, leaving no coat on the core. At that point there is an accelerated release of the active ingredient, and most of the active ingredient is therefore released prior to entry of what is left of the dosage form into the large intestine.

The coating layer on the pharmaceutical composition may contain more than two enteric materials, provided at least two of them have solubilities at different pHs. For instance, the coating may be comprised of two polymers that dissolve at about the same pH in a part of the small intestine, say 5.5, and a third that will dissolve at a different pH in the small intestine, for instance 7.0. A coating can also have three enteric materials each of which will dissolve at a different pH in the small intestine.

The coating layer preferably contains a plasticizer and/or a colorant. The plasticizer improves the flexibility of the coating and reduces cracking of the coating. Plasticizers include, but are not limited to, glycerin, propylene glycol, polyethylene glycols, citrate or phthalate esters, triacetin and acetylated monoglyceride. Colorants are dyes or pigments, and chosen to be compatible with the solvent system used in the coating mixture.

The membrane-controlled pharmaceutical compositions are prepared by coating the dosage form with a mixture of two or more of the enteric materials. The present invention is not limited to a particular method of coating, and several are known and practiced in the art. For instance, the enteric materials can be dissolved in an organic solvent or a mixture of organic solvents. Subsequently, a plasticizer, colorant, or other processing aids can be incorporated into the system. The solvents are commonly chosen from ethyl alcohol, methyl alcohol, acetone, ethyl acetate, methylene chloride, isopropyl alcohol, and methyl ethyl ketone. Another solution employable in the present invention is one where the enteric materials are dissolved in ammonium hydroxide solution; subsequently, a plasticizer, colorant, and possibly other processing aids can be added to the system. Another system is where enteric latex/pseudolatex is diluted with water and then a plasticizer, colorant, and perhaps other processing aids are added.

The cores (coating substrates) can be coated in a fluid-bed apparatus (e.g., Versa-Glatt, available from Glatt Air Technologies) or a side-vented coating pan (e.g. Vector Corp. and O'Hara Technologies) using appropriate air flow, spray rate, and atomization pressure.

The enteric materials are combined into one layer. To have the enteric polymers present in different layers would not serve the purpose of the present invention of a sustained/accelerated profile. This points to another advantage of the present invention, which is a composition that is simpler to prepare.

The compositions of the present invention may be employed to obtain the controlled release and increased bioavailability of any pharmaceutically active ingredient (including nutritional supplements or diagnostic agents) that is compatible with an enteric coating and/or matrix formation with the enteric materials, and with oral delivery. The active ingredients for the pharmaceutical compositions of the present invention can be any one or combination that would benefit from the type of release profile exhibited by the coated cores, although the present invention is not limited thereby. In general, representative types of active ingredients include anti-inflammatories, vasodilators, anti-infectives, psychotropics, anti-depressants, anti-manics, antiparkinsonian substances, anti-hypertensives, agents for the treatment of hyperactivity or attention deficit hyperactivity disorders, vasoconstrictors, stimulants, antiarrythmic agents, antihistamines, decongestants, vitamins, minerals and other nutritional additives, natural medicines such as melatonin, gingko, kava and the like, anti-coagulants, sedatives, anticonvulsants, antispasmodics, thyroid preparations, antiobesity drugs, antiangiogenesis drugs, anticancer agents, contraceptives, hormonal agents, cough suppressants, expectorants, peptide and biopolymeric substances, immunostimulatory agents, and diagnostic agents such as dyes and labeled biomolecules. This list is not exhaustive, and the present invention is not limited in such a way, because it does not rely on the particular activity of the active agent in order to work as intended.

Preferred examples of the foregoing pharmaceutically active agents are one or more selected from morphine sulfate, oxycodone, aspirin, diclofenac, etodolac, indomathacin, ketoprofen, naproxen, metronidazole, nitrofurantoin, erythomycin, procanamide, quinidine sulfate, niacin, propanolol, metoprolol, isradipine, nicardipine, nifedipine, diltiazem, verapamil, isosorbide dinitrate, isosorbide mononitrate, glipizide, potassium chloride, ferrous sulfate, chlopheniramine pseudoephedrine, doxycycline, amoxicillin, amoxicillin/clavulanate potassium, cefaclor, trospium, pyridoxamine, amphetamine, methylphenidate, guanfacine, argylin, alprazolam, carbamazepine, rifampin, trimethoprim, and levodopa/carbidopa.

A more preferred active agent is one selected from amoxicillin, amoxicillin/clavulanate potassium, doxycycline, cefaclor, or rifampin.

In accordance with a second aspect of the present invention, two or more enteric materials are used in forming matrix tablets or beadlets. In general, matrix systems use hydrophilic polymers that swell in the presence of water, or other inert materials such as waxes, to control the release of the pharmaceutically active components from a tablet or capsule. These technologies are well known and have been utilized in the pharmaceutical industry for more than 40 years. The difference in the present invention is that in place of the typical hydrophilic polymers are used two or more of the enteric materials. As with the first aspect of the invention set forth above; the enteric materials are chosen such that they have solubilities at different pHs. In this way, as the dosage form travels through the small intestine, at first one enteric material and then the other(s) will dissolve, thereby releasing the active agent(s) in a controlled manner.

The matrix dosage form according to the invention is provided, for example, as a matrix tablet or bead composed of an effective amount of the active agent or agents distributed or suspended in a controlled release matrix comprised of two or more enteric materials. Examples of suitable enteric materials are cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric).

Generally, the oral matrix dosage forms are prepared using any suitable process known to the art. See, for example, Remington's Pharmaceutical Sciences, $18^{th}$ Edition, A. Gennaro, Ed., Mack Pub. Co. (Easton, Pa. 1990), Chapters 89-91, which is hereby incorporated by reference. Typically, the active ingredient is mixed with the matrix materials and compressed into tablets. Preferably, the dosage form is prepared by combining two or more enteric polymers, at least two of which have solubilities at different pHs, with the active ingredient(s), together with any other excipients that are required for the tableting or the capsule filling of beadlets, using for instance a wet granulation technique or a direct compression method, to form a uniform granulate. Alternatively, the active ingredient(s) can be mixed with the granulate after the granulate is prepared. The moist granulated mass with or without the drug(s) is then dried and sized using a suitable screening device to provide a powder, which can then be filled into capsules or compressed into matrix tablets or caplets, as desired.

More particularly, in a wet granulation method at least one pharmaceutically active agent and the enteric materials and other ingredients are granulated in a granulating fluid (e.g., isopropyl alcohol, ethyl alcohol, and water) in a planetary mixer, high shear mixer, or a fluidized bed granulator. Binding agents may be contained in the granulating fluid or in the dry mix of ingredients. The wet granules are dried in an oven or a fluidized bed dryer, and then sieved through a suitable screen to obtain free flowing granules. The resulting granules may be blended with a suitable lubricant and glidant, and the lubricated granules are compressed into tablets on a rotary press using appropriate tooling.

In the direct compression method, at least one pharmaceutically active agent, the enteric materials and other ingredients are sieved through a stainless steel screen, such as a 40 mesh steel screen. The sieved materials are then charged to a suitable blender and blended for 10 minutes with an intensifier bar for three minutes. The blend is then compressed into tablets on a rotary press using appropriate tooling.

In the above description, "other ingredients" means other substances typically added in formulating tablets and beads, such as bulking agents, disintegrating agents, anti-adherents and glidants, lubricants, and binding agents. These ingredients are very well known. Typical bulking agents include, but are not limited to microcrystalline cellulose (e.g., Avicel®, FMC Corp., Emcocel®, Mendell Incl.), mannitol, xylitol, dicalcium phosphate (eg. Emcompress, Mendell Incl.) calcium sulfate (e.g. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.) The bulking agent may be present in the composition in an amount of from about 5 wt. % to about 90 wt. % preferably from about 10 wt. % to about 50 wt. %.

Disintegrating agents that may be included in the composition include, but are not limited to, microcrystalline cellulose, starches, crospovidone (e.g., Polyplasdone XL, International Specialty Products.), sodium starch glycolate (Explotab, Mendell Inc.), and crosscarmellose sodium (e.g., Ac-Di-Sol, FMC Corp.). The disintegrating agent may be present in the composition in an amount of from about 0.5 wt. % to about 30 wt. %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnauba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount from about 0.2 wt. % to about 10 wt. % preferably from about 0.5 wt. % to about 5 wt. %.

The matrix tablets or beads are preferably coated with an enteric coating (including that of the present invention) when the pharmaceutically active ingredient is sensitive to the enteric environment, or a sustained release coating (including that of the present invention), if further modification of the release profile is desired. Examples of some materials for enteric coatings are set forth previously in the specification.

Examples of sustained release coatings include: waxes mixed with glyceryl monostearate, stearic acid, palmitic acid, glyceryl monopalmitate and cetyl alcohol; shellac and zein; ethylcellulose; acrylic resins; cellulose acetate; and silicone elastomers. The coating of the matrix tablets or beads is done as described above.

A final aspect of the present invention is a method of treating a condition in a mammal, comprising administering to such a mammal an oral dosage form comprising a membrane-controlled or matrix-controlled dosage form of a pharmaceutical ingredient which is active against said condition, and which is coated with a combination of two or more enteric coating materials, whereby the oral dosage form has a drug release profile that is pH-dependent. Preferably, the mammal is a human. More preferably, the condition is a microbial infection and the pharmaceutically active ingredient is an antibiotic. Most preferably, the antibiotic is doxycyline.

EXAMPLES

Example 1

The following is the formula for immediate-release doxycycline beads/pellets:

| | |
|---|---|
| Doxycycline monohydrate | 1.5 kg |
| Hydroxypropyl methylcellulose E5 Premium | 0.113 kg |
| Sugar Spheres, 30/35 mesh | 5.888 kg |
| Purified Water | 5.725 kg |

The beads/pellets were prepared as follows:
1. The drug dispersion was prepared by dispersing the doxycycline monohydrate in purified water containing hydroxypropyl methylcellulose E5 premium as a binder.
2. Sugar seeds (30/35 mesh) were charged into a 9" Wurster Column in a GPCG 15 fluid bed processor.
3. The drug layering dispersion from Step 1 above was sprayed onto the seeds. Spraying was continued until the entire dispersion has been applied.
5. The pellets were dried for 5 minutes after finishing Step 3.
6. The drug-loaded pellets were discharged from the 9" Wurster Column.
7. The doxycycline monohydrate pellets were passed through a 20-mesh screen. The pellets that are less than 20-mesh were collected.

Example 2

Doxycycline pellets from Example 1 were coated in accordance with the present invention. The formula is given below:

| | |
|---|---|
| Doxycycline monohydrate immediate-release pellets | 3.497 kg |
| Eudragit L30D55 | 0.531 kg (1.769 kg liquid) |
| Eudragit FS30D | 0.531 kg (1.769 kg liquid) |
| Triethyl citrate | 0.127 kg |
| Talc | 0.315 kg |
| Opadry white | 0.100 kg |
| Purified water | 3.989 kg |

The coated product is prepared as follows:
1a. The enteric coating dispersion is prepared by adding triethyl citrate, talc, Eudragit L30D55, Eudragit FS30D, to purified water and stirring for about 30 minutes.
1b. The Opadry color coating dispersion is prepared by dispersing Opadry white into purified water.
2. The drug-loaded pellets were charged into the 9" Wurster Column in a GPCG-15 fluid-bed processor.
3. The coating system of Step 1a was sprayed onto the pellets.
4. Continue to spray the enteric coating system until the entire dispersion has been applied.
5. Continue to spray the color dispersion of Step 1b onto the pellets.
6. The coated pellets were dried in the fluid bed processor for 5 minutes after finishing Step 5.
7. The coated pellets were discharged from the 9" Wurster Column.
8. The doxycycline monohydrate pellets were passed through a 20-mesh screen.
9. The pellets that are less than 20-mesh were collected.

Dissolution profiles of doxycycline monohydrate beads coated with a mixture of Eudragit L30D55 and Eudragit FS30D (50:50) at 30% coating level are shown in Table 1. (30% coating level means that 30% of the batch weight is the coating material, which includes the enteric material, plasticizer, and any processing aids.) The enteric coating delayed the drug release in the acidic medium and provided a sustained-release profile (~20% drug release per hour) after exposure to pH 6 medium. Under higher pH testing conditions (e.g., pH 6.5, 7.0, or 7.5), it resulted in the acceleration of the drug release, for example, using pH 6.5 dissolution medium, the drug release was sped up significantly, compared to the dissolution profile at pH 6.0. Furthermore, using pH 7.0 medium, the release of the drug was completed within two hours.

TABLE 1

Dissolution Profiles of Doxycycline Monohydrate Beads Coated with A Mixture of Eudragit L30D55 and Eudragit FS30D (50:50)

| Dissolution medium | Percent Dissolved | | | | | | |
|---|---|---|---|---|---|---|---|
| | 0.5 hour | 1 hour | 2 hours | 2.5 hours | 3 hours | 4 hours | 5 hours |
| Change to pH 6.0 | 0 | 0 | 1 | 14 | 25 | 35 | 50 |
| Change to pH 6.5 | 0 | 0 | 4 | 34 | 52 | 75 | 89 |
| Change to pH 7.0 | 0 | 1 | 2 | — | 64 | 96 | 101 |

Note:
The dissolution medium used in the first two hours was pH 1.1 medium and changed to the specified pH after two hours.

Example 3

The formula of the immediate release beads of this example is as follows:

| | | |
|---|---|---|
| Doxycycline monohydrate immediate-release beads | 500 | grams |
| HPMCP 50 | 32.44 | grams |
| Eudragit L100 | 32.44 | grams |
| Eudragit S100 | 16.22 | grams |
| Triethyl citrate | 7.10 | grams |
| Isopropyl alcohol | 675 | grams |
| Acetone | 675 | grams |

Preparing the beads and coating them was done in a manner analogous to Examples 1 and 2.

Table 2 shows the dissolution profiles of doxycycline monohydrate beads coated with a mixture of hydroxypropyl methylcellulose phthalate 50, Eudragit L100, and Eudragit S100 (40:40:20) at 15% coating level in accordance with this example. Again, the enteric coating delayed the drug release in the acidic medium and provided a sustained-release profile after exposure to pH 6 medium. Using pH 7.0 medium, the drug release was sped up dramatically reaching the complete release within 30 minutes.

TABLE 2

Dissolution Profiles of Doxycycline Monohydrate Beads Coated with A Mixture of Hydroxypropyl Methylcellulose phthalate, Eudragit L100, and Eudragit S100 (40:40:20)

| Dissolution medium | Percent Dissolved | | | | | | |
|---|---|---|---|---|---|---|---|
| | 0.5 hour | 1 hour | 2 hours | 2.5 hours | 3 hours | 4 hours | 5 hours |
| Change to pH 5.0 | 0 | 1 | 1 | 2 | 2 | 2 | 2 |
| Change to pH 6.0 | 0 | 1 | 2 | 3 | 25 | 65 | 87 |
| Change to pH 7.0 | 0 | 1 | 1 | 93 | 93 | 92 | 92 |

Note:
The dissolution medium used in the first two hours was pH 1.1 medium and changed to the specified pH after two hours.

Example 4

The formula for the matrix tablet of this example is as follows:

| | | |
|---|---|---|
| Doxycycline monohydrate powder | 108.10 | grams |
| Eudragit L100 | 88.617 | grams |
| Eudragit S100 | 157.61 | grams |
| HPMCP 50 | 35.448 | grams |
| HPMCP 55 | 35.449 | grams |
| Cellulose acetate phthalate | 35.447 | grams |
| Hydroxypropyl methylcellulose E5 | 12.5 | grams |
| Eudragit FS30D | 10.59 | grams (35.3 grams liquid) |
| Eudragit L30D55 | 10.59 | grams (35.3 grams liquid) |
| Microcrystalline cellulose | 125 | grams |
| Magnesium stearate | 6.25 | grams |

Tablets were prepared as follows:
1. All the dry materials screened through a 60-mesh sieve. All the materials, except for Eudragit FS30D, Eudragit L30D, magnesium stearate, were mixed in a high-shear mixer.
3. The dry blend was wet granulated with the mixture of Eudragit L30D and Eudragit FS30D.
4. The wet granulation is dried in an oven at 40° C.
5. The dried granulation is passed through a 20-mesh screen.
6. Lubricate the blend with magnesium stearate for 3 minutes in a V-shaped blender.
7. The lubricated blend is discharged and the blend is compressed into tablets with a tablet hardness of about 15 to 20 kp and a tablet weight at 250 mg.

Table 3 shows the dissolution profiles of matrix tablet containing doxycycline monohydrate and various enteric materials (e.g., Eudragit L100, Eudragit S100, Hydroxypropyl methylcellulose phthalate, cellulose acetate phthalate, Eudragit L30D55, and Eudragit FS30D) according to the present example. In contrast to the membrane coating approach, doxycycline monohydrate can easily diffuse through a capillary network between the compacted enteric polymer particles in the acidic medium. Under higher pH testing conditions (e.g., pH 6.0 and 7.0), the erosion of the matrix materials becomes a factor influencing the drug dissolution and it resulted in an acceleration of the drug release at the higher pHs.

TABLE 3

Dissolution Profiles of Doxycycline Monohydrate Matrix Tablets Containing A Mixture of Hydroxypropyl Methylcellulose phthalate, Cellulose Acetate Phthalate, Eudragit L30D, Eudragit FS30D, Eudragit L100, and Eudragit S100

| Dissolution medium | Percent Dissolved | | | | | | |
|---|---|---|---|---|---|---|---|
| | 0.5 hour | 1 hour | 2 hours | 2.5 hours | 3 hours | 4 hours | 5 hours |
| Change to pH 5.0 | 24 | 37 | 54 | 60 | 63 | 66 | 68 |
| Change to pH 6.0 | 24 | 37 | 58 | 64 | 68 | 74 | 81 |
| Change to pH 7.0 | 26 | 41 | 66 | 73 | 77 | 85 | 94 |

Note:
The dissolution medium used in the first two hours was pH 1.1 medium and changed to the specified pH after two hours.

What is claimed is:
1. A pharmaceutical composition, comprising:
(a) a core containing one or more pharmaceutically active ingredients selected from one or more of psychotropics, anti-depressants, anti-manics, antiparkinsonian substances, agents for the treatment of hyperactivity or attention deficit hyperactivity disorders, stimulants, sedatives, anticonvulsants, and antispasmodics, and
(b) a coating layer surrounding the core, said coating layer comprising a combination of three or more enteric coating materials selected from the group consisting of cellulose acetate phthalate; hydroxypropyl methylcellulose phthalate; polyvinyl acetate phthalate; hydroxypropyl methylcellulose acetate succinate; cellulose acetate trimellitate; copolymer of methylvinyl ether and maleic anhydride; zein; methacrylic acid copolymers; acrylate copolymers; hydroxypropyl methylcellulose phthalate/poly(methacrylic acid-co-methyl methacrylate) 1:1/poly(methacrylic acid-co-methyl methacrylate) 1:2; hydroxypropyl methylcellulose phthalate/cellulose acetate phthalate/poly(methacrylic acid-co-methyl methacrylate) 1:2; hydroxypropyl methylcellulose phthalate/cellulose acetate phthalate/poly(methacrylic acid-co-methyl methacrylate 1:1/poly(methacrylic acid-co-methyl methacrylate) 1:2; polyvinyl acetate phthalate/cellulose acetate trimellitate/zein/poly(methacrylic acid-co-methyl methacrylate) 1:2, at least two of which enteric coating materials dissolve at a different pH in the small intestine,
wherein the active ingredient(s) has a release profile that is pH-dependent,
wherein the release profile is at first sustained while the composition is in a part of the small intestine of a first pH and then accelerated when the composition is in a part of the small intestine of a second pH, and wherein said first pH is lower than said second pH, and
wherein more than 70% of the active ingredient(s) is dissolved prior to entering the large intestine.
2. The pharmaceutical composition of claim 1, wherein the coating layer comprises three or more enteric coating materials each of which dissolves at a different pH.

3. The pharmaceutical composition of claim 1, wherein the coating layer also comprises a plasticizer and/or a colorant.

4. The formulation of claim 1, wherein said coating layer additionally comprises a sustained release coating material.

5. The pharmaceutical composition of claim 1, wherein the oral dosage form is a tablet, a capsule, beads, beadlets or sachet.

6. The pharmaceutical composition of claim 1, wherein the active pharmaceutical ingredient is one or more of morphine sulfate, oxycodone, amphetamine, methylphenidate, guanfacine, alprazolam, carbamazepine, and levodopa/carbidopa.

7. A method of treating a CNS condition in a mammal, comprising administering to a mammal in need thereof an oral dosage form according to claim 1.

8. The method of claim 7, wherein the mammal is a human.

9. A pharmaceutical composition, comprising:
   (a) a core containing one or more pharmaceutically active ingredients selected from one or more of psychotropics, anti-depressants, anti-manics, antiparkinsonian substances, agents for the treatment of hyperactivity or attention deficit hyperactivity disorders, stimulants, sedatives, anticonvulsants, and antispasmodics, and
   (b) a coating layer surrounding the core, said coating layer comprising:
      (i) a combination of two or more enteric coating materials selected from the group consisting of cellulose acetate phthalate; hydroxypropyl methylcellulose phthalate; polyvinyl acetate phthalate; hydroxypropyl methylcellulose acetate succinate; cellulose acetate trimellitate; copolymer of methylvinyl ether and maleic anhydride; zein; methacrylic acid copolymers; acrylate copolymers; hydroxypropyl methylcellulose phthalate/poly(methacrylic acid-co-methyl methacrylate 1:1/poly(methacrylic acid-co-methyl methacrylate) 1:2; hydroxypropyl methylcellulose phthalate/cellulose acetate phthalate/poly(methacrylic acid-co-methyl methacrylate) 1:2; hydroxypropyl methylcellulose phthalate/cellulose acetate phthalate/poly(methacrylic acid-co-methyl methacrylate 1:1/poly(methacrylic acid-co-methyl methacrylate) 1:2; polyvinyl acetate phthalate/cellulose acetate trimellitate/zein/poly(methacrylic acid-co-methyl methacrylate) 1:2, at least two of which enteric coating materials dissolve at a different pH, and
      (ii) a sustained release coating material,
   wherein the active ingredient(s) has a release profile that is pH-dependent,
   wherein the release profile is at first sustained while the composition is in a part of the small intestine of a first pH and then accelerated when the composition is in a part of the small intestine of a second pH, and wherein said first pH is lower than said second pH, and
   wherein more than 70% of the active ingredient(s) is dissolved prior to entering the large intestine.

10. A method of treating a CNS condition in a mammal, comprising administering to a mammal in need thereof an oral dosage form according to claim 9.

11. The method of claim 10, wherein the mammal is a human.

12. The pharmaceutical composition of claim 1, wherein the first pH is between 5.0-6.5.

13. The pharmaceutical composition of claim 1, wherein the second pH is between 6.0-7.5.

* * * * *